(12) United States Patent
Quaedflieg et al.

(10) Patent No.: US 7,018,817 B1
(45) Date of Patent: *Mar. 28, 2006

(54) PROCESS FOR THE PREPARATION OF COMPOUNDS WITH ENHANCED OPTICAL PURITY

(75) Inventors: Peter Jan Leonard Mario Quaedflieg, Geleen (NL); Theodorus Sonke, Guttecoven (NL); Adolf Fritz Volker Wagner, Ludwigsburg (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/869,088

(22) PCT Filed: Dec. 17, 1999

(86) PCT No.: PCT/NL99/00783

§ 371 (c)(1),
(2), (4) Date: Jun. 19, 2001

(87) PCT Pub. No.: WO00/37657

PCT Pub. Date: Jun. 29, 2000

(30) Foreign Application Priority Data

Dec. 22, 1998 (EP) ................... 98204371

(51) Int. Cl.
*C12P 21/06* (2006.01)
*C12P 13/22* (2006.01)
(52) U.S. Cl. .................. 435/108; 435/109; 435/129
(58) Field of Classification Search ............. 435/68.1, 435/108, 109, 129
See application file for complete search history.

(56) References Cited

U.S. PATENT DOCUMENTS 6,617,127 B1 * 9/2003 Quaedflieg et al. ......... 435/68.1

OTHER PUBLICATIONS

Patel et al., 1997, CAS:126:277722.*
Groche et al., Biochem. Biophys. Res. Comm. (1998) 246: 342-346.
Rajagopalan et al., Biochemistry (1997) 36:13910-13918.
Wagner et al., J. Biol. Chem. (1998) 273:11413-11416.

* cited by examiner

*Primary Examiner*—Taofiq Solola
*Assistant Examiner*—Robert Shiao
(74) *Attorney, Agent, or Firm*—Morrison & Foerster LLP

(57) ABSTRACT

Process for the preparation of a compound with enhanced optical purity wherein a mixture of the enantiomers of a chiral compound of formula 1

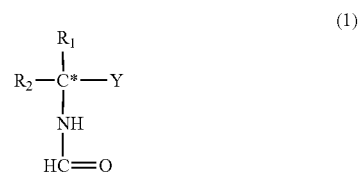

wherein:
$R_1$ represents an alkyl or an aryl group
$R_2$ represents H, an alkyl or an aryl group
Y represents an alkyl group, an aryl group, $(CH_2)_n COOH$, $(CH_2)_n$—COOR, $(CH_2)_n$—CONRR', $CH_2OH$, or C≡N wherein R and
R' independently represent H, an alkyl or aryl group, and n represents 0 or 1, is brought into contact with an enzyme having peptide deformylase activity with a bivalent metal ion as a cofactor wherein the metal is chosen from the groups 5–11 of the periodic system, or for the preparation of a formylated compound with enhanced optical purity from a mixture of the enantiomers of the corresponding not formulated chiral compound in the presence of a formylation agent.

Preferably the peptide deformylase is chosen from the class EC 3.5.2.27 or EC 3.5.1.31, and contains the sequences of (I) HEXXH, (ii) EGCLS and (iii) GXGXAAXQ. The bivalent metal may be chosen from the group of Fe, Ni, Mn and Co, preferably Ni or Fe.

9 Claims, No Drawings

PROCESS FOR THE PREPARATION OF COMPOUNDS WITH ENHANCED OPTICAL PURITY

CROSS-REFERENCE TO RELATED APPLICATIONS

This Application is the national phase of PCT application PCT/NL99/00783, filed 17 Dec. 1999, which claims priority from European application 98/204371.3 filed 22 Dec. 1998. The contents of these applications are incorporated herein by reference.

The invention relates to a process for the preparation of a compound with enhanced optical purity wherein a mixture of the enantiomers of a chiral compound of formula 1:

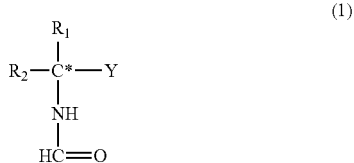

wherein:
$R_1$ represents an optionally substituted alkyl or an optionally substituted aryl group
$R_2$ represents H, an optionally substituted alkyl or an optionally substituted arylgroup
Y represents an alkyl group, an aryl group, $(CH_2)_n COOH$, $(CH_2)_n$—COOR, $(CH_2)_n$—CONRR', $CH_2OH$, or C≡N wherein R and R' independently represent H, an alkyl or aryl group, and n represents 0 or 1, is brought into contact with an enzyme having peptide deformylase activity with a bivalent metal ion as a cofactor wherein the metal is chosen from the groups 5–11 of the periodic system.

Enzymes having peptide deformylase activity are known in the literature e.g. from P. T. Ravi Rajagopalan et al., Biochemistry 1997, 36, 13910–13918 wherein the use of peptide deformylase is described for the deformylation of several peptides with N-formylmethionine at the N-terminus and of N-formylmethionine. Although the known peptide deformylases showed reasonable deformylase activity when peptides where used as a substrate, they showed no or little activity with respect to N-formylmethionine.

Applicant surprisingly found that the peptide deformylases having a bivalent metal ion as a cofactor according to the invention, did not only show a considerable activity towards the substrates according to formula 1, but also appeared to be enantioselective. U.S. Pat. No. 4,745,067 discloses L-aminoacylases which exhibit enantioselective activity towards N-acyl-L-amino acids. However, the activity of these enzymes towards N-formyl-L-methionine is low.

The alkyl groups in $R_1$, $R_2$, R, $R^1$ en Y may be cyclic or linear or branched chains. The alkyl, aryl and the methylene groups may be substituted. Suitable substituents are for instance, hydroxy, alkyl, alkoxy, e.g. methoxy, mercapto, alkylmercapto, amino, guanyl, carboxamide, halogen, e.g. chloro, aryl, e.g. phenyl and hydroxyphenyl, imidazolyl or indonyl.

Substrates according to formula 1 that can be used in the process of the invention are for instance amino acids, for instance α- or β-amino acids with 1–20 C-atoms, in particular α-H-α-amino acids, α-methyl-α-amino acids, β-amino acids; esters of said amino acids wherein the ester group is for instance an alkyl group having 1–10 C-atoms; amides of said amino acids, wherein optionally the amide is N-substituted with 1 or 2, preferably 1, substituent chosen from alkyl or aryl, having 1–10 C-atoms; nitriles corresponding to said α-amino acids; amino alcohols corresponding to said α-amino acids; or amines for instance (optionally substituted) aromatic or aliphatic amines. Suitable substituents are for instance (optionally substituted) alkyl groups, for instance with 1–10 C-atoms.

In another embodiment of the present invention a mixture of the enantiomers of a (non protected) amino compound is subjected to a formylation in the presence of a peptide deformylase having a bivalent metal ion as a cofactor, wherein the metal is chosen from the groups 5–11 of the periodic system and a formylating agent, whereby one of the enantiomers is selectively converted into the corresponding N-formyl amino compound.

Suitable formylating agents are for instance formic acid in case a thermodynamically controlled formylation can be performed, or formic acid esters or amides when the formylation is kinetically controlled. In a thermodynamically controlled formylation the equilibrium is shifted towards the side of formyl derivative, preferably by precipitation of the formyl derivative.

Peptide deformylases are in general enzymes having formyl methionine peptide deformylase activity. The peptide deformylases to be used according to the invention have a more than 10 times, preferably more than 100 times, in particular more than 1000 times, higher activity towards the formyl protected compounds according to formula 1 compared to the corresponding acetyl protected compounds. Activity here is defined as the catalytic efficiency (also called: specificity constant) $K_{cat}/K_m$ expressed in $M^{-1} sec^{-1}$; wherein $K_m$ (expressed in mM) represents the Michaelis constant (this is the substrate concentration at which the reaction rate is 50% of the maximum reaction rate observed) and $K_{cat}$ (expressed in $min^{-1}$) represents the turnover number. It should be noticed that in the literature also other names are being used instead of the name Peptide deformylases; in particular the following names may be mentioned here: formylmethionine deformylase, N-formylmethionyl aminoacyl-tRNA deformylase, N-formyl-L-methionine amidohydrolase N-formylmethionyl-aminoacyl-tRNA amidohydrolase.

Suitable peptide deformylases to be used in the process according to the invention are peptide deformylases classified as EC 3.5.1.27. Preferably, the enzyme is an enzyme having the activity as described for EC 3.5.1.27 because excellent results are being achieved in the deformylation with such enzymes. It should be noticed, that until recently it was believed that the enzyme coded as EC 3.5.1.31 is catalyzing a different reaction. In the meantime however it has been shown that the enzymes known as EC 3.5.1.27 and EC 3.5.1.31 are coded for by exactly the same gene and have the same activity. Therefore, as used herein, the term EC 3.5.1.27 is encompassing not only EC 3.5.1.31, but likewise all other enzymes having the same activity as described for EC 3.5.1.27.

Although the family of PDF's is composed of proteins with a relatively low level of sequence identity, the 3D structures of the members of this family appear closely related one to each other with, in particular, the building of a common fold around the bivalent metal ion and three signature sequences. As is described (for PDF's indicated as PDF) by Wagner et al., J. Biol. Chem., 273, 11413–6 (1998), for many of these enzymes characteristically three short amino acid stretches are present as strictly conserved motifs, namely in that the contain the sequences (i) HEXXH (SEQ ID NO:1), (ii) EGCLS (SEQ ID NO:2) and (iii) GXGX-AAXQ (SEQ ID NO:3). In these sequences X represents any natural amino acid, and standard one letter codes for amino acids are used: A=alanine, C=cysteine, E=glutamic acid, G=glycine, H=histidine, L=leucine, S=serine and Q=glutamine.

Peptide deformylases are obtainable for instance from eubacteria for example *Escherichia coli, Bacillus subtilis, Clostridium acetobutylicum Clostridium beyerinckii, Haemophilus influenzae Thermotoga maritima, Thermus aquaticus, Thermus thermophilus*, Calothrix PCC 7601, *Bacillus stearothermophilus* or *Lactococcus lactis*. Preferably an enzyme of *Escherichia Coli* is used.

The peptide deformylases according to the invention require a bivalent metal ion whereby the metal is chosen from the groups 5–11 of the periodic system (New IUPAC version; see Handbook of Chemistry and Physics 70th edition, CRC Press, 1989–1990, inner page of cover), as a cofactor. Preferably the metal is chosen from the group of V, Cr, Fe, Ni, Mn, Co, Cu, Pd and Pt, in particular from the group of Fe, Ni, Mn and Co.

Preferably the amount of the bivalent metal ions should be about equivalent to the number of moles of enzyme. Suitably the molar ratio between these bivalent metal ions and the number of PDF molecules is in the range of 0.6 to 1.4, preferably of 0.8 to 1.2, and most preferred the amount of bivalent metal ions is equimolar to the enzyme.

Exchange of the bivalent metal ions in the PDF's in order to obtain PDF enzymes with a co-factor as necessary for the present invention can be done by the various methods as described in Groche et al., Biochem. Biophys. Res. Comm., 246, 342–346, (1998). These methods include simple metal displacement by incubation of the native enzyme in an excess of the desired bivalent metal ion, if necessary preceeded by the preparation of the apoenzyme via treatment of the native enzyme with a metal chelation compound. Furthermore, the desired bivalent metal ion can already be introduced in (at least part of the enzyme molecules) by using a bacterial growth medium with an enhanced ratio of the desired bivalent metal ion over $Fe^{2+}$.

In addition measures may be taken in order to enhance the stability of the enzyme, for instance the addition of stabilisation agents, for instance catalase, tris-(2-carboxyethyl) phosphine, glucose oxidase, or combinations thereof; or enlarging the concentration of the PDF, for instance to a PDF concentration of at least 0.1 mg of PDF per ml, more preferably of least 1.0 mg/ml. The upper limit of the concentration of PDF is not critical if practical concentrations are being used. The use of stabilisation measures is especially preferred when an easily oxidisable metal ion, e.g. $Fe^{++}$ is present as a cofactor or an easily oxidisable substrate. If not, for instance in case $Ni^{++}$ is present as a cofactor the addition of a stabilisation agent appeared to be superfluous, as the enzyme turned out to be very stable even without stabilisation agent.

The enzymes applied in the process according to the invention may be purified enzymes, a crude enzyme solution, microbial cells exhibiting the required activity, a homogenate of cells or permeabilized cells. If required, the enzyme may be applied in an immobilized state or in a chemically modified form to ensure a good stability, reactivity and enantioselectivity of the enzymes under the conditions utilized.

Alternatively, genetically engineered mutants of PDF's may be used which have for instance enhanced activity or enantioselectivity in the (de)formylation reaction. These mutants can be generated by a number of different approaches; for instance, by site-directed mutagenesis, site-specific random mutagenesis, regio-specific random mutagenesis, and completely random mutagenesis; the latter form of mutagenesis is better known as directed evolution. General applicable methods to perform these different protein engineering approaches are well known to the skilled man. If a random approach will be applied, the mutagenesis cycle will need to be followed by selection of resistent and active mutant(s), thereby leading to the identification of suitable mutants. To obtain PDF mutants also a combination of different protein engineering approaches and/or several rounds of random mutagenesis may be used.

The reaction conditions for the enzymatic deformylation according to the invention are not very critical and may depend on the substrate used. Any suitable solvent system which is inert towards the PDF may be applied; such solvents include aqueous systems (solutions or slurries) or aqueous systems also containing a water-miscible organic solvent which is inert under the reaction conditions. Aqueous systems, however, are preferred. Also the concentration of the N-formyl compound is not critical, and may be for instance in the range of about 0.1 to 1000 mM. It is not necessary that all of the N-formyl compound is dissolved; part of it may be present as a slurry. The concentration of the PDF likewise is not very critical, and usually will be at 0.001 to 100% by weight of the formyl compound, e.g. at about 0.2 mM of PDF. The pH for the reaction preferably is chosen in the range of 4.0 to 11.0, more preferably of 5.0 to 10.0. The temperature is not very critical, and suitably will be in the range of 10 to 50° C., e.g. at about 37° C., but for thermostable PDF enzymes higher temperatures may be applied.

In those cases wherein the absolute configuration of the (de)formylated enantiomer was determined, it appeared that the S-enantiomer was (de)formylated more rapidly than the R-enantiomer. The optical purity is given by the enantiomeric excess (ee), the enantioselectivity of the enzyme is represented by E, and calculated as $k_f/k_s$ wherein $k_f$ is defined as the rate of (de)formylation of the most rapidly (de)formylated enantiomer and $k_s$ is defined as the rate of (de)formylation of the least rapidly (de)formylated enantiomer.

Optionally a salt promoting hydrophobic interactions is added to the reaction mixture, for instance a sulphate, phosphate, sulphite or acetate of ammonium, Rb, K, Na, Cs or Li. Most preferably ammonium sulphate or lithium sulphate is used.

The invention will further be elucidated by the following examples, without being limited thereto.

Abbreviations:

| | |
|---|---|
| TB medium: | 12 g/l of Bacto-Tryptone, Difco; 24 g/l of yeast extract, Difco; 4 g/l of glycercole; 2.3 g/l of $KH_2PO_4$; 12.5 g/l of $K_2HPO_4$); |
| Hepes: | N-2-hydroxyethylpiperazine-N'-2-ethane sulphuric acid; |
| AEBSF: | 2-aminoethyl-p-benzene sulphonyl fluoride; |
| TCEP: | tris-(2-carboxyethyl)-phosphine. |
| MOPS: | 3-(N-morpholino)propane sulphonic acid |
| MES: | 2-(N-morpholino)ethane sulphonic acid |

EXAMPLES 1–15

Comparative Experiments A and B

Isolation of PDF(Fe)

For a detailed discussion of the methods used reference is made to Groche et al., BBRC 246, 342–346 (1998).

PDF(Fe) was isolated from overproducing E. coli cells grown at 30° C. in 1.6 l TB medium for 14–16 h. About 13 g (wet weight) cell paste were suspended in 26 ml buffer (20 mM Hepes/KOH, 100 mM KF, pH 7.7 supplemented with 10 µg/ml catalase from bovine liver (Boehringer Mannheim) and 1 mM AEBSF, disintegrated by sonication (Branson B12, 20 min) at 0° C. and centrifuged at 200.000 g for 1 h. The clear supernatant (1.3 g of protein; according to biurete reaction) was mixed with 1.3 ml 10% (w/v) Polymin G-35 (BASF) adjusted to pH 7.7 and centrifuged at 40.000 g for 10 min. The supernatant was applied to a 20 ml Met-Lys-Sepharose column that had been equilibrated with 20 mM Hepes/KOH, 100 mM KF, 0.2 mM TCEP, pH 7.7. After washing with 120 ml of 20 mM Hepes/KOH, 100 mM KF, 0.2 mM TCEP, pH 7.7, PDF(Fe) was eluted with 150 ml 20 mM Hepes/KOH, 100 mM KCl, 0.2 mM TCEP, pH 7.7. The protein containing fractions were concentrated by ultrafiltration using an Amicon PM10 membrane (yield: 140 mg protein, 1400 U/mg; determined according to Groche et al.). After adjustment of the TCEP concentration to 1 mM and protein concentration to 40 mg/ml, the PDF(Fe) stock solution (40 mg/ml=2 mM) was stored frozen at −60° C. After thawing, the PDF(Fe) stock solution could be used directly in the deformylation experiments described below. If however solutions with lower PDF(Fe) concentrations were required for these deformylation experiments, the PDF stock solution was diluted further in 20 mM Hepes/KOH, pH 7.7, 100 mM KCl, 1 mg/ml bovine serum albumin, 10 µg/ml catalase solution.

HPLC-Analysis

In all cases HPLC conditions had to be developed in which the two deformylated isomers were separated from each other and from the formylated isomers. To this end two different techniques were applied that is method 1 and method 2, as described below.

From the quantities of deformylated isomers in the samples after various reaction times, both the initial deformylation rate constant ($k_f$ and $k_s$ in $M^{-1}s^{-1}$) could be calculated for both enantiomers, as well as the respective ee values. The enantioselectivity of the enzyme (E value) was calculated by taking the ratio of $k_f/k_s$ and is given for all Examples in table 1, as well as the maximum ee value ($ee_{max}$) observed during the experiments.

Method 1 (Without Derivatization)

A Crownpak CR(+) column (4×150 mm) was used. Samples (5 µl) withdrawn from the deformylation mixture were mixed with 95 µl aqueous $HClO_4$ (10 mM) to inactivate PDF(Fe). Following a brief centrifugation, 20 µl of the supernatant were applied to the Crownpak CR(+) column. For specific chromatographic conditions and retention times see table 2.

Method 2 (Precolumn derivatization with o-phthaldialdehyde (OPA) and N-acetyl-L-cysteine (NAC). Samples (25 µl) withdrawn from the deformylation mixture were mixed with 25 µl aqueous $HClO_4$ (100 mM) to inactivate PDF(Fe). Following a brief centrifugation, 40 µl of the supernatant were added to 80 µl 1 M aqueous $H_3BO_3$/NaOH pH 9.4, subsequently 20 µl OPA reagent (consisting of OPA in $H_2O/CH_3OH$ 1:1 v/v with a concentration as indicated in table 3) and 20 µl NAC reagent (consisting of NAC in $H_2O/CH_3OH$ 1:1 v/v with a concentration as indicated in table 3) was added. After the time indicated in table 3 derivatization was terminated by addition of 80 µl (250 mM) aqueous $H_3PO_4$, and 20 µl of the solution were instantaneously applied to a Nucleosil 120-5 $C_{18}$ (250×4 mm) column. Temperature was always ambient and detection was spectrophotometric using a wavelength of 257 nm and/or 340 nm. The used eluent was a mixture of aqueous 0.05 M $H_3PO_4$ brought at pH 7.0 with 1 M NaOH, and a percentage of acetonitrile as indicated in table 3. For derivatization of valine aminonitrile borate buffer was adjusted to pH 11 and addition of NAC reagent was done 10 min after OPA reagent had been added. Concentration of $H_3PO_4$ used for termination was 500 mM. Derivatization and separation conditions as well as the observed retention times for the deformylated compounds analyzed are compiled in table 3.

Examples 1–12 and comparative experiments A and B were executed according to the procedures A, B, or C as given below as indicated in table 1. The results of the examples and comparative experiments are summarized in table 1 and the corresponding HPLC conditions in tables 2 and 3.

Method A

Deformylation in the Presence of $Li_2SO_4$ at pH 7.2

Deformylation reactions were performed in 1.5 ml Eppendorf reaction test tubes. The reaction mixture with a total volume of 200 µl contained 100 mM aqueous MOPS/NaOH, 2 M $Li_2SO_4$ buffer pH 7.2, and the concentration of formylated compound as indicated in table 1. After thermal equilibration to 37° C. the deformylation reaction was started by the addition of the concentration of PDF as indicated in table 1. At various reaction times samples of the reaction mixture were withdrawn in which the reaction was stopped by addition of $HClO_4$.

Method B

Deformylation in the Absence of $Li_2SO_4$ at pH 7.2

Reactions were performed as described in Method A with the exception that 100 mM aqueous MOPS/NaOH, 250 mM NaCl, 0.1 mg/ml catalase buffer pH 7.2 was used in stead of 100 mM aqueous MOPS/NaOH, 2 M $Li_2SO_4$ buffer pH 7.2.

Method C

Deformylation in the Absence of $Li_2SO_4$ at pH 6.2

Reactions were performed as described in Method A with the exception that 100 mM aqueous MES/NaOH buffer pH 6.2 was used in stead of 100 mM MOPS/NaOH, 2 M $Li_2SO_4$ buffer pH 7.2.

TABLE 1

Results of deformylation experiments

| Ex. | Compound | Type of compound | Method | [Compound] (mM) | [PDF] (µM) | $k_s$ ($M^{-1}s^{-1}$) | $k_f$ ($M^{-1}s^{-1}$) | E | $ee_{max}$ (%) |
|---|---|---|---|---|---|---|---|---|---|
| 1 | N-formyl-phenylglycine | α-H-amino acid | B | 10 | 200 | 0.0047 | 10,6 | 2255 | 99,6 |
| 2 | N-formyl-3-amino-3-phenyl-propionic acid | β-H-amino acid | B | 10 | 10 | <0.004 | 7,1 | >1775 | 100 |
| 3 | N-formyl-phenylglycine amide | α-H-amino acid amide | B | 10 | 5.2 | 0.09 | 227 | 2522 | 99,7 |

TABLE 1-continued

Results of deformylation experiments

| Ex. | Compound | Type of compound | Method | [Compound] (mM) | [PDF] (μM) | $k_s$ (M$^{-1}$s$^{-1}$) | $k_f$ (M$^{-1}$s$^{-1}$) | E | ee$_{max}$ (%) |
|---|---|---|---|---|---|---|---|---|---|
| 4 | N-formyl-tert-leucine amide | α-H-amino acid amide | A | 4.8 | 200 | 0.0005 | 0,15 | 300 | 100 |
| 5 | N-formyl-α-methyl-phenylglycine amide | α-alkyl-amino acid amide | A | 10 | 200 | 0.0005 | 0,045 | 90 | 100 |
| 6 | N-formyl-phenylglycinol | β-amino alcohol | B | 10 | 200 | 0.029 | 0,69 | 23,8 | 90,5 |
| 7 | N-formyl-phenylglycinol | β-amino alcohol | A | 10 | 200 | 0.34 | 6,3 | 18,5 | 93,3 |
| 8 | N-formyl-alaninol | β-amino alcohol | A | 10 | 200 | 0.018 | 0,22 | 12 | 85,6 |
| 9 | N-formyl-phenylalanine aminonitrile | α-aminonitrile | C | 7.5 | 20 | 1 | 880 | 880 | 98,8 |
| 10 | N-formyl-valine aminonitrile | α-aminonitrile | A | 10 | 50 | 0.62 | 29,7 | 47,9 | 95,5 |
| 11 | N-formyl-m-methoxy-phenylalanine aminonitrile | α-aminonitrile | B | 7.2 | 2.5 | 2 | 1370 | 685 | 99,0 |
| 12 | N-formyl-1-(1-naphthyl)-ethylamine | amine | A | 0.42 | 200 | 0.03 | 0,45 | 15 | 90 |
| A | N-acetyl-phenylglycine amide | α-H-amino acid amide | A | 10 | 10 | <0.001 | <0,001 | — | — |
| B | N-formyl-proline | α-H-imino acid | A | 10 | 200 | <0.004 | <0,004 | — | — |

TABLE 2

Analytical conditions and retention times analyzed according to method 1

| Ex. | Compound | Eluent | flow rate (ml/min) | T (° C.) | Detection (nm) | retention time (min) Amine | Amine | formyl-compound |
|---|---|---|---|---|---|---|---|---|
| 1 | N-formyl-phenylglycine | 10 mM aq. HClO$_4$ | 1.0 | 40 | 210 | 2.1 (D) | 3.8 (L) | 9.6 |
| 2 | N-formyl-3-amino-3-phenyl-propionic acid | 85% 100 mM aq. HClO$_4$/15% CH$_3$OH | 0.7 | 5 | 210 | 23.7 | 26.7 | 11.4 |
| 3 | N-formyl-phenylglycine amide | 10 mM aq. HClO$_4$ | 0.8 | 22 | 210 | 3.2 (D) | 12.6 (L) | 6.3 |
| 6/7 | N-formyl-phenylglycinol | 95% 10 mM aq. HClO$_4$/5% CH$_3$OH | 0.8 | 5 | 210 | 4.8 (L) | 5.7 (D) | 10.0 |
| 9 | N-formyl-phenylalanine aminonitrile | 90% 10 mM aq. HClO$_4$/10% CH$_3$OH | 0.8 | 5 | 210 | 11.8 | 15.1 | 28.6 |
| 11 | N-formyl-m-methoxy-phenylalanine aminontrile | 90% 10 mM aq. HClO$_4$/10% CH$_3$OH | 0.8 | 5 | 210 | 23.8 | 30.7 | 52.0 |
| 12 | N-formyl-1-(1-naphthyl)-ethylamine | 85% 10 mM aq. HClO$_4$/15% CH$_3$OH | 1.0 | 40 | 210 | 26.5 (S) | 31.2 (R) | 73.5 |
| A | N-acetylphenylglycine amide | 10 mM aq. HClO$_4$ | 0.8 | 22 | 210 | 3.2 (D) | 12.6 (L) | 6.9 |
| B | N-formyl-proline | 100 mM aq. HClO$_4$ | 0.4 | 5 | 200 | 3.8 | 3.8 | 5.7 |

TABLE 3

Analytical conditions and retention times analyzed according to method 2

| Ex. | Compound | OPA (mg/ml) | NAC (mg/ml) | Time (min.) | % CH$_3$CN | Retention Time (min.) Amine | Amineformyl |
|---|---|---|---|---|---|---|---|
| 2 | N-formyl-3-amino-3-phenyl propionic acid | 4 | 4 | 30 | 15 | 19.7 | 23.3 |
| 4 | N-formyl-tert-leucine amide | 8 | 8 | 10 | 22.5 | 14.9 (D) | 17.4 (L) |
| 5 | N-formyl-α-methyl-phenylglycine amide | 16 | 16 | 30 | 20 | 24.4 | 26.3 |
| 8 | N-formyl-alaninol | 4 | 4 | 5 | 15 | 16.9 (L) | 18.8 (D) |
| 10 | N-formyl-valine aminonitrile | 16 | 4 | 5 | 20 | 8.6 (L) | 10.2 (D) |

What is claimed is:

1. A process for the preparation of a compound with enhanced optical purity which comprises contacting a mixture of the enantiomers of a chiral compound of formula 1

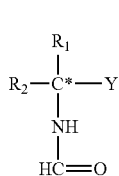

(1)

wherein:
$R_1$ represents an alkyl or an aryl group
$R_2$ represents H, an alkyl or an aryl group
Y represents an alkyl group, an aryl group, $(CH_2)_n COOH$, $(CH_2)_n$—COOR, $(CH_2)_n$—CONRR', $CH_2OH$, or C≡N wherein R and R' independently represent H, an alkyl or aryl group, and n represents 0 or 1, with an enzyme which is a peptide deformylase and with a bivalent metal ion as a cofactor, wherein the metal is a metal of the groups 5–11 of the periodic system, wherein one of the enantiomers is selectively deformylated, and wherein the compound with enhanced optical purity is of the formula

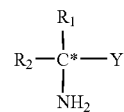

wherein $R_2$, $R_1$ and Y are as in the compound of formula (1).

2. The process of claim 1, wherein the peptide deformylase is of the class EC 3.5.2.27 or EC 3.5.1.31.

3. The process of claim 1, wherein the peptide deformylase contains the sequences of (i) HEXXH (SEQ ID NO:1), (ii) EGCLS (SEQ ID NO:2) and (iii) GXGXAAXQ (SEQ ID NO:3).

4. The process of claim 1, wherein the peptide deformylase is obtainable from *Escherichia coli*.

5. The process of claim 1, wherein the bivalent metal is Fe, Ni, Mn or Co.

6. The process of claim 5, wherein the bivalent metal is Ni.

7. The process of claim 1, which further comprises adding a stabilisation agent.

8. The process of claim 7 wherein the stabilisation agent is catalase.

9. The process of claim 7 wherein the bivalent metal is Fe.

* * * * *

SEQUENCE LISTING

<160> NUMBER OF SEQ ID NOS: 3

<210> SEQ ID NO 1
<211> LENGTH: 5
<212> TYPE: PRT
<213> ORGANISM: Unknown
<220> FEATURE:
<223> OTHER INFORMATION: Strictly conserved motif of peptide deformylase
<221> NAME/KEY: VARIANT
<222> LOCATION: (1)...(5)
<223> OTHER INFORMATION: Xaa = Any Amino Acid

<400> SEQUENCE: 1

His Glu Xaa Xaa His
 1               5

<210> SEQ ID NO 2
<211> LENGTH: 5
<212> TYPE: PRT
<213> ORGANISM: Unknown
<220> FEATURE:
<223> OTHER INFORMATION: Strictly conserved motif of peptide deformylase

<400> SEQUENCE: 2

Glu Gly Cys Leu Ser
 1               5

<210> SEQ ID NO 3
<211> LENGTH: 8
<212> TYPE: PRT
<213> ORGANISM: Unknown
<220> FEATURE:
<223> OTHER INFORMATION: Strictly conserved motif of peptide deformylase
<221> NAME/KEY: VARIANT
<222> LOCATION: (1)...(8)
<223> OTHER INFORMATION: Xaa = Any Amino Acid

<400> SEQUENCE: 3

Gly Xaa Gly Xaa Ala Ala Xaa Gln
 1               5